US009168182B2

(12) United States Patent
Hargett et al.

(10) Patent No.: US 9,168,182 B2
(45) Date of Patent: Oct. 27, 2015

(54) METHOD AND APPARATUS FOR ATTACHING ELASTIC COMPONENTS TO ABSORBENT ARTICLES

(71) Applicant: The Procter & Gamble Company, Cincinnati, OH (US)

(72) Inventors: Mark Mason Hargett, Liberty Township, OH (US); Paul Anthony Kawka, Guilford, IN (US); Raymond Scott Hamilton, Lebanon, OH (US); Bradley Edward Walsh, Cincinnati, OH (US); Terry Howard Thomas, Deerfield Township, OH (US); Jon Kevin McLaughlin, West Chester, OH (US); David Carlton Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 197 days.

(21) Appl. No.: 13/929,854

(22) Filed: Jun. 28, 2013

(65) Prior Publication Data

US 2014/0000798 A1    Jan. 2, 2014

Related U.S. Application Data

(60) Provisional application No. 61/665,930, filed on Jun. 29, 2012.

(51) Int. Cl.
*A61F 13/15* (2006.01)
*A61F 13/49* (2006.01)

(52) U.S. Cl.
CPC ..... *A61F 13/15699* (2013.01); *A61F 13/15593* (2013.01); *A61F 13/15756* (2013.01); *Y10T 156/1002* (2015.01)

(58) Field of Classification Search
CPC ............... Y10T 156/1011; Y10T 156/1015; Y10T 156/1051; Y10T 156/1052; B65H 2801/57; B32B 2555/02; A61F 13/15593; A61F 13/15601; A61F 13/49011; A61F 13/49012; A61F 13/49019; A61F 2013/4905
USPC ............... 156/164, 229, 494, 495, 496
See application file for complete search history.

(56) References Cited

U.S. PATENT DOCUMENTS 3,848,594 A    11/1974  Buell
3,860,003 A    1/1975   Buell
(Continued)

FOREIGN PATENT DOCUMENTS

EP    0 565 606 B1    3/1995
EP    2 332 505 A1    6/2011
(Continued)

OTHER PUBLICATIONS

PCT/International Search Report, dated Sep. 30, 2013, 11 pages.
(Continued)

*Primary Examiner* — Carson Gross
(74) *Attorney, Agent, or Firm* — Sarah M. DeCristofaro; Abbey A. Lopez

(57) ABSTRACT

A first substrate advances in the first direction and a second substrate advances in the second direction. The first substrate advances onto an outer circumferential surface of a drum in a stretched state. The first substrate may be cut into discrete lengths of elastic substrate. The drum may be configured with vacuum to hold the discrete length of elastic substrate in a stretched state. The second substrate may advance in the second direction by a conveyor. The conveyor includes a roller having a curved outer surface that deforms the second substrate so as to define a curve in the first direction. A tamper apparatus intermittently displaces a deformed portion of the second substrate into contact with a discrete length of elastic substrate on the outer circumferential surface of the drum. The discrete length of elastic substrate bonds with the second substrate and is removed from the drum.

17 Claims, 12 Drawing Sheets

(56) References Cited

U.S. PATENT DOCUMENTS

| | | | |
|---|---|---|---|
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,381,781 A | 5/1983 | Sciaraffa et al. | |
| 4,463,045 A | 7/1984 | Ahr et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,785,996 A | 11/1988 | Ziecker et al. | |
| 4,795,454 A | 1/1989 | Dragoo | |
| 4,808,178 A | 2/1989 | Aziz et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,888,231 A | 12/1989 | Angstadt | |
| 4,894,060 A | 1/1990 | Nestegard | |
| 4,909,803 A | 3/1990 | Aziz et al. | |
| 4,925,520 A | 5/1990 | Beaudoin et al. | |
| 4,946,527 A | 8/1990 | Battrell | |
| 4,963,140 A | 10/1990 | Robertson et al. | |
| 4,988,344 A | 1/1991 | Reising et al. | |
| 4,988,345 A | 1/1991 | Reising | |
| 5,006,394 A | 4/1991 | Baird | |
| 5,026,450 A * | 6/1991 | Cucuzza et al. | 156/244.11 |
| 5,137,537 A | 8/1992 | Herron et al. | |
| 5,147,345 A | 9/1992 | Young et al. | |
| 5,151,092 A | 9/1992 | Buell et al. | |
| 5,221,274 A | 6/1993 | Buell et al. | |
| 5,260,345 A | 11/1993 | Desmarais et al. | |
| 5,342,338 A | 8/1994 | Roe | |
| 5,387,207 A | 2/1995 | Dyer et al. | |
| 5,518,801 A | 5/1996 | Chappell et al. | |
| 5,562,646 A | 10/1996 | Goldman et al. | |
| 5,571,096 A | 11/1996 | Dobrin et al. | |
| 5,580,411 A | 12/1996 | Nease et al. | |
| 5,595,567 A | 1/1997 | King et al. | |
| 5,624,427 A | 4/1997 | Bergman et al. | |
| 5,643,396 A | 7/1997 | Rajala et al. | |
| 5,650,222 A | 7/1997 | Desmarais et al. | |
| 5,669,894 A | 9/1997 | Goldman et al. | |
| 5,674,216 A | 10/1997 | Buell et al. | |
| 5,691,035 A | 11/1997 | Chappell et al. | |
| 5,693,165 A | 12/1997 | Schmitz | |
| 5,723,087 A | 3/1998 | Chappell et al. | |
| 5,735,840 A | 4/1998 | Kline et al. | |
| 5,745,922 A | 5/1998 | Rajala et al. | |
| 5,865,823 A | 2/1999 | Curro | |
| 5,916,663 A | 6/1999 | Chappell et al. | |
| 5,928,212 A | 7/1999 | Kline et al. | |
| 5,941,864 A | 8/1999 | Roe | |
| 6,004,306 A | 12/1999 | Roe et al. | |
| 6,010,491 A | 1/2000 | Roe et al. | |
| 6,027,483 A | 2/2000 | Chappell et al. | |
| 6,251,097 B1 | 6/2001 | Kline et al. | |
| 6,414,215 B1 | 7/2002 | Roe | |
| 6,432,098 B1 | 8/2002 | Kline et al. | |
| 6,441,266 B1 | 8/2002 | Dyer et al. | |
| 6,494,244 B2 | 12/2002 | Parrish et al. | |
| 6,573,423 B1 | 6/2003 | Herrlein et al. | |
| 6,596,108 B2 | 7/2003 | McCabe | |
| 6,677,258 B2 | 1/2004 | Carroll et al. | |
| 7,195,684 B2 * | 3/2007 | Satoh | 156/163 |
| 7,569,039 B2 | 8/2009 | Matsuda et al. | |
| 7,811,403 B2 | 10/2010 | Andrews | |
| 8,377,249 B2 | 2/2013 | Gill | |
| 2004/0162536 A1 | 8/2004 | Becker et al. | |
| 2004/0167486 A1 | 8/2004 | Busam et al. | |
| 2005/0107764 A1 | 5/2005 | Matsuda et al. | |
| 2005/0215972 A1 | 9/2005 | Roe et al. | |
| 2005/0215973 A1 | 9/2005 | Roe et al. | |
| 2005/0275148 A1 | 12/2005 | Beaudoin et al. | |
| 2006/0083893 A1 * | 4/2006 | Ashraf | 428/131 |
| 2006/0148358 A1 * | 7/2006 | Hall et al. | 442/328 |
| 2006/0189956 A1 | 8/2006 | Vatansever | |
| 2007/0078427 A1 | 4/2007 | Raycheck et al. | |
| 2007/0093769 A1 | 4/2007 | Kline et al. | |
| 2007/0142798 A1 | 6/2007 | Goodlander et al. | |
| 2007/0142806 A1 | 6/2007 | Roe et al. | |
| 2007/0219521 A1 | 9/2007 | Hird et al. | |
| 2007/0287348 A1 | 12/2007 | Autran et al. | |
| 2007/0287982 A1 | 12/2007 | Lodge et al. | |
| 2007/0287983 A1 | 12/2007 | Autran et al. | |
| 2008/0132865 A1 | 6/2008 | Li et al. | |
| 2009/0099542 A1 | 4/2009 | Oomman et al. | |
| 2009/0294044 A1 * | 12/2009 | Gill et al. | 156/256 |
| 2009/0299314 A1 * | 12/2009 | Middlesworth et al. | 604/367 |
| 2010/0108268 A1 | 5/2010 | Yamamoto et al. | |
| 2010/0252603 A1 | 10/2010 | Gill | |
| 2011/0094669 A1 | 4/2011 | Oetjen | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2012/0061015 A1 | 3/2012 | LaVon et al. | |
| 2012/0061016 A1 | 3/2012 | LaVon et al. | |
| 2012/0330263 A1 | 12/2012 | Lawson et al. | |

FOREIGN PATENT DOCUMENTS

| | | |
|---|---|---|
| EP | 2 446 868 A1 | 5/2012 |
| EP | 2 460 645 A1 | 6/2012 |
| EP | 2 554 145 A1 | 2/2013 |
| WO | WO 95/16746 | 6/1995 |
| WO | WO 96/24319 A1 | 8/1996 |
| WO | WO 00/02727 A1 | 1/2000 |
| WO | WO 2005/035414 A1 | 4/2005 |
| WO | WO 2006/015141 | 2/2006 |
| WO | WO 2009/027892 A1 | 3/2009 |
| WO | WO 2009/083791 A1 | 7/2009 |
| WO | WO 2009/146307 A1 | 12/2009 |

OTHER PUBLICATIONS

U.S. Appl. No. 13/929,843, filed Jun. 28, 2013, Bradley Edward Walsh.
U.S. Appl. No. 13/929,857, filed Jun. 28, 2013, Mark Mason Hargett.
U.S. Appl. No. 13/929,863, filed Jun. 28, 2013, Mark Mason Hargett.
U.S. Appl. No. 13/929,869, filed Jun. 28, 2013, Raymond Scott Hamilton.
U.S. Appl. No. 13/929,878, filed Jun. 28, 2013, Raymond Scott Hamilton.

* cited by examiner

METHOD AND APPARATUS FOR ATTACHING ELASTIC COMPONENTS TO ABSORBENT ARTICLES

This application claims priority to U.S. Provisional Application Ser. No. 61/665,930, filed Jun. 29, 2012, which is hereby incorporated by reference in its entirety.

FIELD OF THE INVENTION

The present disclosure relates to methods and apparatuses for manufacturing disposable absorbent articles, and more particularly, methods and apparatuses for attaching components, such as waistbands, side panels, cuffs, or other components to disposable absorbent articles.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final cut to separate the web(s) into discrete diapers or other absorbent articles. The discrete diapers or absorbent articles may also then be folded and packaged.

Various methods and apparatuses may be used for attaching different components to the advancing web. Some processes join elastic components such as waistbands to an advancing web. The waistbands may be joined to the advancing web in a stretched condition. In some processes, the components advance in a first direction and are joined with a continuous length of absorbent articles advancing a second direction. In some processes, the waistband material may be advanced in a first direction, stretched, rotated, and advanced in a second direction before being applied to an advancing web. However, rotating and advancing the waistband material in the second direction before attaching the waistband material to an advancing web adds cost and complexity to manufacturing processes. Therefore, it may be beneficial to provide a simplified method and apparatus for joining components advancing in a first direction to absorbent articles advancing in a second direction without rotating and advancing the components in the second direction.

SUMMARY OF THE INVENTION

Aspects of the present disclosure involve a method for applying discrete lengths of a first substrate to a second substrate, the method comprising the steps of: rotating a drum about an axis of rotation, the drum having an outer circumferential surface, wherein the outer circumferential surface has a contour; advancing a first substrate in a first direction; stretching the first substrate along the first direction; advancing the stretched first substrate onto the outer circumferential surface of the drum; cutting the stretched first substrate into discrete lengths of substrate while advancing on the outer circumferential surface of the drum, wherein each discrete length includes a first end region, a second end region, and a central region separating the first and second end regions; advancing a second substrate in a second direction, wherein the second direction crosses the first direction; deforming a portion of the second substrate along the first direction to define a curve extending along the first direction; repeatedly displacing the deformed portion of the second substrate into contact with the discrete lengths of substrate on the outer circumferential surface of the drum; and bonding the discrete lengths of substrate to the second substrate.

Aspects of the present disclosure involve an apparatus for applying discrete lengths of a first substrate to a second substrate. The apparatus may comprise a drum rotatable about an axis of rotation. The drum has an outer circumferential surface and a plurality of vacuum apertures on the outer circumferential surface of the drum for advancing a first substrate in a first direction. The outer circumferential surface of the drum has a contour. The apparatus may comprise a cutter positioned adjacent to the drum and configured to cut the first substrate into a plurality of discrete lengths of substrate as the first substrate advances on the outer circumferential surface of the drum. The apparatus may also comprise a conveyor for advancing the second substrate in a second direction in close proximity to, but not in contact with, the drum. The conveyor comprises a roller having an outer surface. The outer surface of the roller has a curved shape that corresponds with at least a portion of the contour of the outer circumferential surface of the drum so as to deform a portion of the second substrate. The apparatus may comprise a tamper member positioned adjacent the drum to displace the deformed portion of the second substrate into contact with a discrete length of substrate on the outer circumferential surface of the drum.

DETAILED DESCRIPTION OF THE INVENTION

Figure 1:
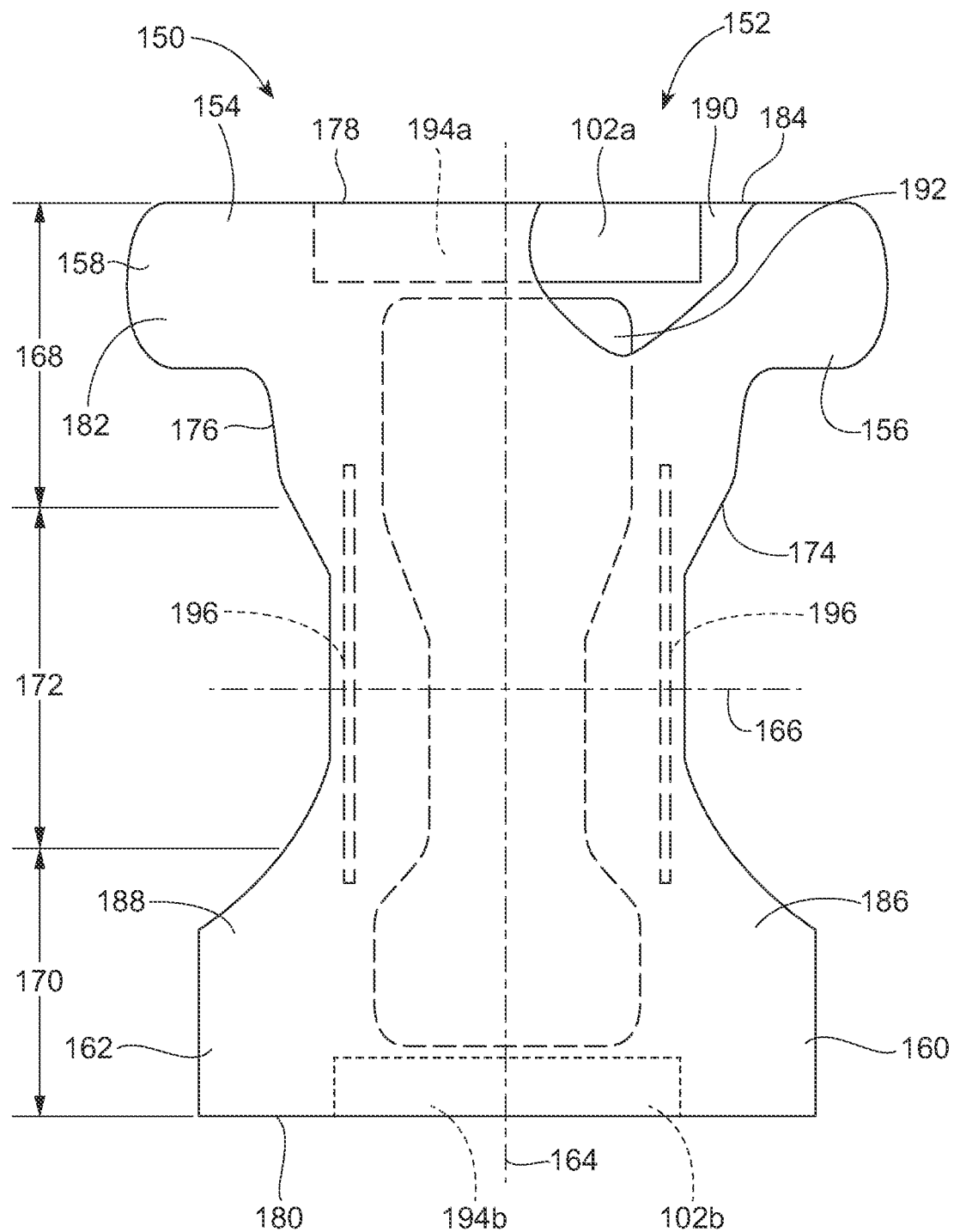
FIG. 1 is a partially cut-away, plan view of a disposable absorbent article having discrete lengths of elastic substrate in the form of elastic waistbands.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to the material's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers bonded together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is not parallel with, and usually perpendicular to, the machine direction.

An "elastic," "elastomer" or "elastomeric" refers to any material that upon application of a force to the material's relaxed, initial length can stretch or elongate to an elongated length more than 10% greater than the material's initial length and will substantially recover back to about the material's initial length upon release of the applied force. The term "inelastic" refers herein to any material that does not fall within the definition of "elastic".

The term "stretchable" is used herein to refer to materials that are capable of extending in at least one direction to a certain degree without undue rupture.

"Radial" means a direction running from an axis of rotation of a drum toward the outer circumferential surface of the drum.

"Vacuum pressure" refers to a pressure applied to a discrete length of a first substrate from radially inward from an outer circumferential surface of a drum. Vacuum pressure is a pressure below atmospheric air pressure.

"Consolidation" and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic strand having a relaxed length of 100 millimeters would have a length of 250 millimeters at 150% elongation. An elastic strand having a relaxed length of 100 millimeters would have a length of 180 millimeters at 80% elongation.

Aspects of the present disclosure involve methods for manufacturing absorbent articles, and more particularly, methods for applying stretched, discrete lengths of elastic substrate such as waistbands to an advancing second substrate during the manufacture of disposable absorbent articles. The methods and apparatuses disclosed herein provide for simplified processes as well as other beneficial results associated with joining stretched waistbands advancing in the first direction to absorbent articles advancing in a second direction. While the present disclosure relates mainly to addition of elastic components such as elastic waistbands to diapers, it is to be appreciated that the methods and apparatuses disclosed herein may also be applied to other elastic or inelastic components used on diapers as well as other types of absorbent articles. For example, elastic components can include pre-stretched ears or side panels, leg cuffs, and elastic topsheets. In addition, other applications may include the addition of various inelastic components such as backsheets, topsheet, absorbent cores, front and/or back ears, and fastener components.

The joining process disclosed herein may include the step continuously advancing a first substrate in a first direction and continuously advancing a second substrate in a second direction. The first substrate may advance onto an outer circumferential surface of a drum in a stretched state. The outer circumferential surface of the drum may have a contour. Adhesive may be applied to the first substrate before the first substrate advances onto the drum. The first substrate may be cut into discrete lengths of elastic substrate such as elastic waistbands while advancing on the outer circumferential surface of the drum. The drum may be configured with vacuum to hold the discrete lengths of elastic substrate on the drum in a stretched state once the discrete lengths of elastic substrate are cut from the advancing first substrate. From the drum, the discrete lengths of elastic substrate are joined with the advancing second substrate.

The second substrate may advance in the second direction by a conveyor. The conveyor may be configured to periodically slow or stop the movement of the second substrate in the machine direction in order to join the discrete lengths of elastic substrate to the second substrate. The conveyor may include a roller having a curved outer surface. The curved shape of the outer surface of the roller may correspond with at least a portion of the contour of the outer circumferential surface of the drum. As the second substrate advances in the second direction by the conveyor, the second substrate is deformed in the first direction so as to define a curve in the first direction that corresponds with at least a portion of the contour of the outer circumferential surface of the drum. Concurrently, while the second substrate is stopped in the machine direction, the tamper apparatus moves the deformed second substrate into contact with a discrete length of elastic substrate on the drum. As a result, the discrete length of elastic substrate is joined to the second substrate in a stretched state. The tamper apparatus then moves away from the second substrate and the second substrate continues advancing in the machine direction with the discrete length of elastic substrate attached thereto.

For the purposes of a specific illustration, FIG. 1 shows an example of a disposable absorbent article 150 in the form of a diaper 152 that may be constructed according to the methods and apparatuses disclosed herein. In particular, FIG. 1 is a plan view of one embodiment of a diaper 152 including a chassis 154 shown in a flat, unfolded condition, with the portion of the diaper 152 that faces a wearer oriented towards the viewer. A portion of the chassis structure is cut-away in FIG. 1 to more clearly show the construction of and various features that may be included in embodiments of the diaper.

As shown in FIG. 1, the diaper 152 includes a chassis 154 having a first ear 156, a second ear 158, a third ear 160, and a fourth ear 162. To provide a frame of reference for the present discussion, the chassis is shown with a longitudinal axis 164 and a lateral axis 166. The chassis 154 is shown as having a first waist region 168, a second waist region 170, and a crotch region 172 disposed intermediate the first and second waist regions. The periphery of the diaper is defined by a pair of longitudinally extending side edges 174, 176; a first outer edge 178 extending laterally adjacent the first waist region 168; and a second outer edge 180 extending laterally adjacent the second waist region 170. As shown in FIG. 1, the chassis 154 includes an inner, body-facing surface 182, and an outer, garment-facing surface 184. A portion of the chassis structure is cut-away in FIG. 1 to more clearly show the construction of and various features that may be included in the diaper. As shown in FIG. 1, the chassis 154 of the diaper 152 may include an outer covering layer 186 including a topsheet 188 and a backsheet 190. An absorbent core 192 may be disposed between a portion of the topsheet 188 and the backsheet 190. As discussed in more detail below, any one or more of the regions may be stretchable and may include an elastomeric material or laminate as described herein. As such, the diaper 152 may be configured to adapt to a specific wearer's anatomy upon application and to maintain coordination with the wearer's anatomy during wear.

As previously mentioned, the chassis 154 of the diaper 152 may include the backsheet 190, shown for example, in FIG. 1. In some embodiments, the backsheet is configured to prevent exudates absorbed and contained within the chassis from soiling articles that may contact the diaper, such as bedsheets and undergarments. Some embodiments of the backsheet may be fluid permeable, while other embodiments may be impervious to liquids (e.g., urine) and comprises a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films. Suitable breathable composite materials are described in greater detail in PCT Application No. WO 95/16746, published on Jun. 22, 1995 in the name of E.I. DuPont and U.S. Pat. No. 5,865,823. Other breathable backsheets including nonwoven webs and apertured formed films are described in U.S. Pat. Nos. 5,571,096 and 6,573,423.

The backsheet 190, or any portion thereof, may be stretchable in one or more directions. In one embodiment, the backsheet may comprise a structural elastic-like film ("SELF") web. Embodiments of SELF webs are more completely described in U.S. Pat. Nos. 5,518,801; 5,723,087; 5,691,035; 5,916,663; and 6,027,483. In some embodiments, the backsheet may comprise elastomeric films, foams, strands, nonwovens, or combinations of these or other suitable materials with nonwovens or synthetic films. Additional embodiments include backsheets that comprise a stretch nonwoven material; an elastomeric film in combination with an extensible nonwoven; an elastomeric nonwoven in combination with an extensible film; and/or combinations thereof. Details on such backsheet embodiments are more completely described in U.S. Publication Nos. US2007/0287348A1; US2007/0287982A1; and US2007/0287983A1. The backsheet 190 may be joined with the topsheet 188, the absorbent core 192, and/or other elements of the diaper 152 in various ways. For example, the backsheet may be connected with a uniform continuous layer of adhesive, a patterned layer of adhesive, or an array of separate lines, spirals, or spots of adhesive. One embodiment utilizes an open pattern network of filaments of adhesive as disclosed in U.S. Pat. No. 4,573,986. Other embodiments utilize several lines of adhesive filaments which are swirled into a spiral pattern, as is illustrated by the apparatus and methods shown in U.S. Pat. Nos. 3,911,173; 4,785,996; and 4,842,666. In some embodiments, the backsheet is connected with heat bonds, pressure bonds, ultrasonic bonds, dynamic mechanical bonds, or any other suitable attachment means or a combination thereof.

The topsheet 188 may be constructed to be compliant, soft feeling, and non-irritating to the wearer's skin. Further, all or at least a portion of the topsheet 188 may be liquid pervious, permitting liquid to readily penetrate therethrough. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006,394. Other topsheets may be made in accordance with U.S. Pat. Nos. 4,609,518 and 4,629,643.

In some embodiments, the topsheet 188 is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345. A more detailed discussion of some methods for incorporating surfactant in the topsheet can be found in U.S. Statutory Invention Registration No. H1670, which was published on Jul. 1, 1997, in the names of Aziz et al. In some embodiments, the topsheet 188 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215.

The absorbent core 192 may include absorbent material that is generally compressible, conformable, non-irritating to the wearer's skin, and capable of absorbing and retaining liquids such as urine and other body exudates. The absorbent core 192 can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures are described in U.S. Pat. Nos. 4,610,678; 4,673,402; 4,834,735; 4,888,231; 5,137,537; 5,147,345; 5,342,338; 5,260,345; 5,387,207; and 5,650,222.

The absorbent core 192 may also have a multiple layered construction. A more detailed discussion of various types of multi-layered absorbent cores can be found in U.S. Pat. Nos. 5,669,894; 6,441,266; and 5,562,646; European Patent No. EP0565606B1; U.S. Patent Publication No. 2004/0162536A1; 2004/0167486A1; and PCT Publication No. WO 2006/015141. In some embodiments, the absorbent article includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to collect forces tending to move the article on the wearer.

Although the first and second ears 156, 158 as well as the third and fourth ears 160, 162 shown in FIG. 1 are illustrated as being integrally formed with the chassis 154, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306. The ears may also include various geometries and arrangements of stretch zones or elements, such as discussed in U.S. Pat. Publication Nos. US2005/0215972A1 and US2005/0215973A1.

As shown in FIG. 1, the diaper 152 may include leg cuffs 196 that may provide improved containment of liquids and other body exudates. The leg cuffs 196 may be disposed in various ways on the diaper 152. For example, the leg cuffs 196 may be disposed on the outer, garment-facing surface 184 of the chassis 154; the inner, body-facing surface 182; or between the inner and outer facing surfaces. Leg cuffs 196 may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs). U.S. Pat. Nos. 4,695,278 and 4,795,454 describe disposable diapers having dual cuffs, including gasketing cuffs and barrier cuffs. In some embodiments, it may be desirable to treat all or a portion of the leg cuffs with a lotion, as described above. In addition to leg cuffs, diaper can also include an elastic gasketing cuff with one or more elastic strands positioned outboard of the barrier cuff. The leg cuffs may be treated with a hydrophobic surface coating, such as described in U.S. Pat. Publication No. 2006/0189956A1.

The diaper 152 may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274. Additional examples of fasteners and/or fastening elements are discussed in U.S. Pat. Nos. 6,251,097 and 6,432,098; and U.S. Patent Publication Nos. 2007/0078427 and 2007/0093769. Other fastening systems are described in more detail in U.S. Pat. Nos. 5,595,567; 5,624,427; 5,735,840; and 5,928,212. The fastening system may also provide a means for holding the article in a disposal configuration as disclosed in U.S. Pat. No. 4,963,140.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The diaper 152 may also include one or more discrete lengths of elastic substrate 102a and 102b, shown in FIG. 1 in the form of a waistband 194a and 194b. The discrete length of elastic substrate 102 may be configured to elastically expand and contract to dynamically fit the wearer's waist to provide improved fit and waste containment. The discrete length of elastic substrate 102 can be incorporated into the diaper 152 in accordance with the methods discussed herein and may extend at least longitudinally outwardly from the absorbent core 192 and generally form at least a portion of the first and/or second outer edges 178, 180 of the diaper 152. In addition, the discrete length of elastic substrate 102 may extend laterally to include the ears. While the discrete length of elastic substrate 102 or any constituent elements thereof may comprise one or more separate elements affixed to the diaper 152, the discrete length of elastic substrate 102 may be constructed as an extension of other elements of the diaper, such as the backsheet 190, the topsheet 188, or both the backsheet and the topsheet. In addition, the discrete length of elastic substrate 102 may be disposed on the outer, garment-facing surface 184 of the chassis 154; the inner, body-facing surface 182; or between the inner and outer facing surfaces. The discrete length of elastic substrate 102 may be constructed in a number of different configurations including those described in U.S. Patent Publication Nos. 2007/0142806; 2007/0142798; and 2007/0287983.

Figure 2C:
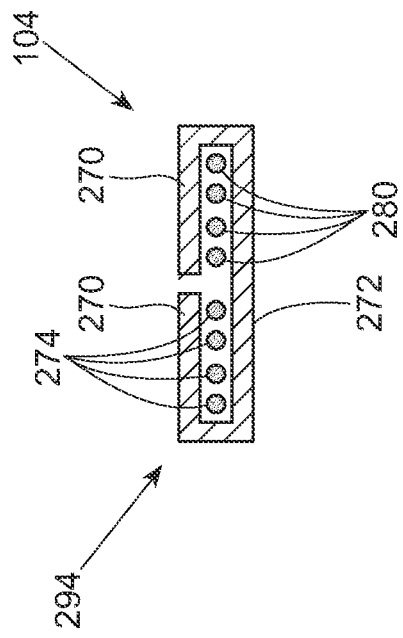
FIG. 2B-2D are schematic, sectional views of a first substrate having a single continuous substrate and an elastic material.
Figure 2D:
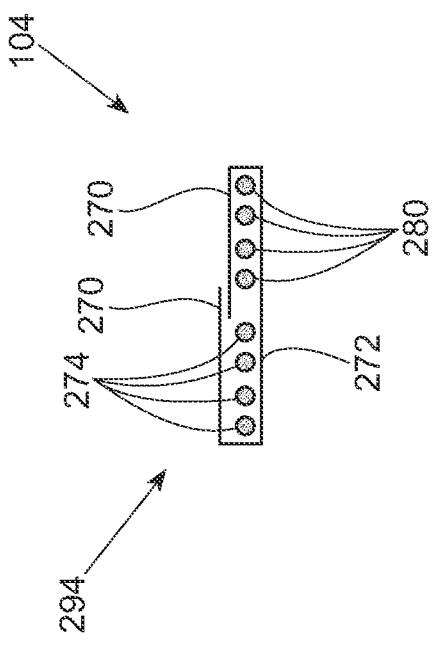
Figure 2A:
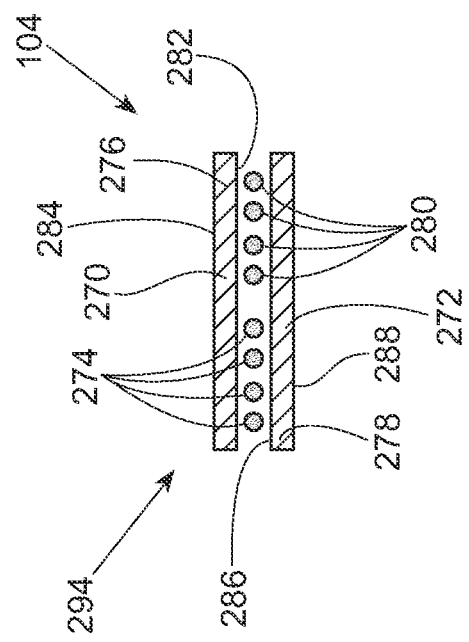
FIG. 2A is a schematic, sectional view of a first substrate having first and second continuous substrate layers and an elastic material.
Figure 2B:
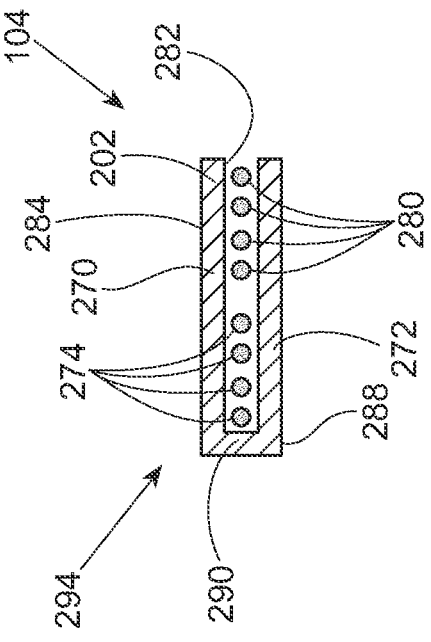

As discussed in more detail below, the elastic waistbands 194a and 194b may be cut from a first substrate 104, shown in FIGS. 2A-2D in the form of a layered elastic substrate 294 for purposes of illustration. The first substrate 104 may include a first substrate layer 270 and a second substrate layer 272 joined with an elastic material 274. In some exemplary configurations, the first substrate layer 270 may be formed from a first continuous substrate layer 275, and the second substrate layer 272 may be formed from a second continuous substrate layer 277 as shown in FIG. 2A. The elastic material 274 may be in the form of elastic strands 280 such as shown in FIGS. 2A-2D. However, it is to be appreciated that the elastic material 274 may be in the form of elastic strands, ribbons, films, or combinations thereof. The first substrate layer 270 may be defined by a first surface 282 and an opposing second surface 284. The second substrate layer 272 may be defined by a first surface 286 and an opposing second surface 288. The elastic material 274 may be located between the first surface 282 of the first substrate layer 270 and the first surface 286 of the second substrate layer 272. In other exemplary configurations, the first substrate layer 270 and/or the second substrate layer 272 may be formed from a single continuous substrate 290 as shown in FIGS. 2B-2D.

It is to be appreciated that the first substrate 104 may include various materials and may be arranged in various configurations. For example, the first and/or second substrate layers 270 and/or 272 and may include woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some exemplary configurations, the first and/or the second substrate layers may include a polymeric film (e.g., polyethylene or polypropylene). In some exemplary configurations, the first and/or second substrate layers 270 and/or 272 may include a stretchable material. Exemplary layered elastic substrates are described in U.S. Provisional Patent Application 61/665,942, titled "Apparatus and Method for Making a Layered Elastic Substrate," filed Jun. 29, 2012 and U.S. Provisional Patent Application 61/665,945, titled "Apparatus and Method for Making a Layered Elastic Substrate," filed Jun. 29, 2012.

Figure 3A:
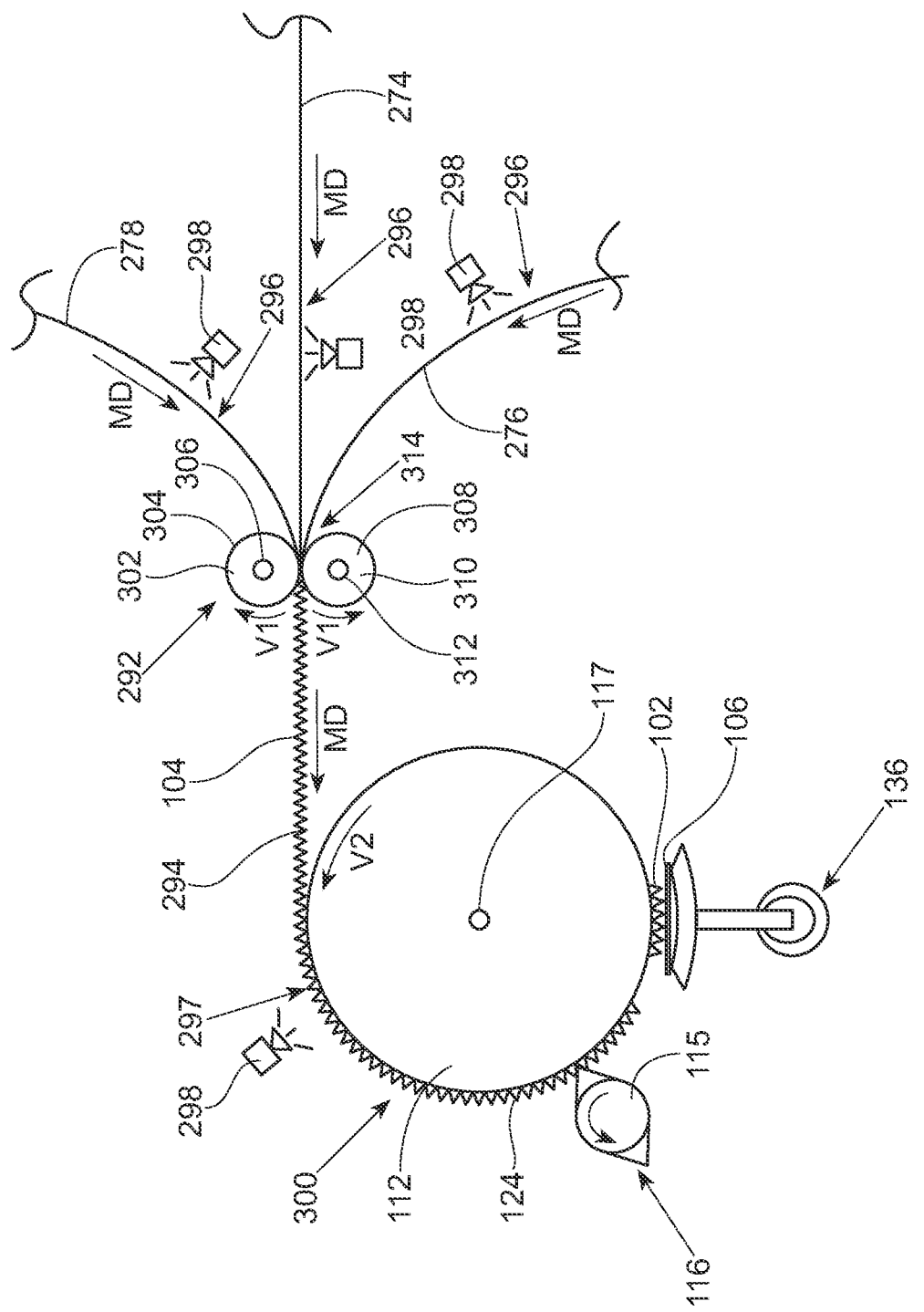
FIG. 3A is a schematic, side view of a process for forming a first substrate.

FIG. 3A shows an exemplary process for forming the first substrate 104. As shown in FIG. 3A, a continuous length of elastic material 274 in a stretched state and continuous lengths of first and second substrate layers 270 and 272 and are advanced in the machine direction MD to a first metering device 292. The elastic material 274 may be joined with first and second substrate layers 270 and 272 at the first metering device 292 to form the first substrate 104, shown in the form of a continuous length of layered elastic substrate 294 for purposes of illustration. As shown in FIG. 3A, adhesive 296 may be applied to the first substrate layer 270, the second substrate layer 272, and the elastic material 274 by an adhesive applicator 298 before advancing through the first metering device 292. From the first metering device 292, the first substrate 104 may advance in the machine direction MD to a second metering device 300. As discussed in more detail below, the first substrate 104 is consolidated between the first and second metering devices 292 and 300 from a first elongation to a second elongation that is less than the first elongation. Exemplary processes for forming a layered elastic substrate are described in U.S. Provisional Patent Application 61/665,942, titled, "Apparatus and Method for Making a Layered Elastic Substrate," filed Jun. 29, 2012 and U.S. Provisional Patent Application 61/665,945, titled "Apparatus and Method for Making a Layered Elastic Substrate," filed Jun. 29, 2012; and U.S. Provisional Application 61/666,087, titled, System and Method For High-Speed Continuous Application of a Strip Material To A Moving Sheet-Like Substrate Material," filed Jun. 29, 2012.

Figure 3B:
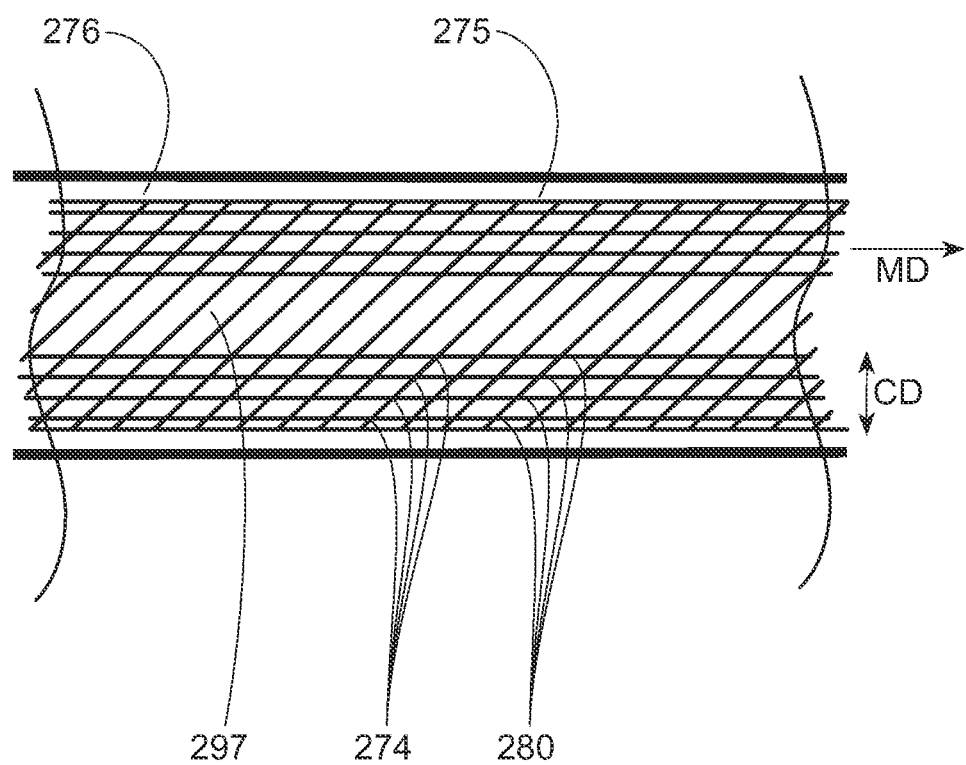
FIG. 3B is a schematic, plan view of a first substrate layer having adhesive for bonding elastic strands to the first substrate layer.

In some exemplary configurations, adhesive 297 may be applied to portions of the first and second substrate layers 270 and 272. For example, FIG. 3B shows a first substrate layer 270 bonded with an elastic material 274, shown in the form of a first continuous substrate layer 275 bonded with elastic strands 280 for purposes of illustration. As shown in FIG. 3B, adhesive 297 (represented by cross-hatched areas) may be applied to only a portion of the first substrate layer 270 such that the adhesive does not cover the entire surface of the first substrate layer 270.

It is to be appreciated that the metering devices may be configured in various ways. For example, the first metering device 292 shown in FIG. 3A includes a first roller 302 having an outer circumferential surface 304 and rotatable about a first axis of rotation 306 and a second roller 308 having an outer circumferential surface 310 and rotatable about a second axis of rotation 312. The first roller 302 and the second roller 308 rotate in opposite directions, and the second roller 308 is adjacent the first roller 302 to define a first nip 314 between the first roller 302 and the second roller 308. The first and second rollers 302 and 308 rotate such that the outer circumferential surfaces 304 and 310 have a surface speed V1. The second metering device 300 shown in FIG. 3A includes a drum 112 having an outer circumferential surface 124 and rotatable about an axis of rotation 117. The drum 112 rotates such that the outer circumferential surface 124 has a surface speed V2. Upstream of the first nip 286, the first substrate 104 may advance at a surface speed V1 or less. Because the first substrate 104 is advancing at surface speed V1 at the first nip 286 and is advancing at surface speed V2 at the drum 272, wherein V2 is less than V1, the first substrate 104 consolidates in the machine direction MD from a first elongation to a second elongation that is less than the first elongation. As a result, gathers form in the first substrate 104 as shown in FIG. 3A. Exemplary metering devices are described in U.S. Provisional Patent Application 61/665,942, titled "Apparatus and Method for Making a Layered Elastic Substrate," filed Jun. 29, 2012 and U.S. Provisional Patent Application 61/665,945, titled "Apparatus and Method for Making a Layered Elastic Substrate," filed Jun. 29, 2012.

Figure 4A:
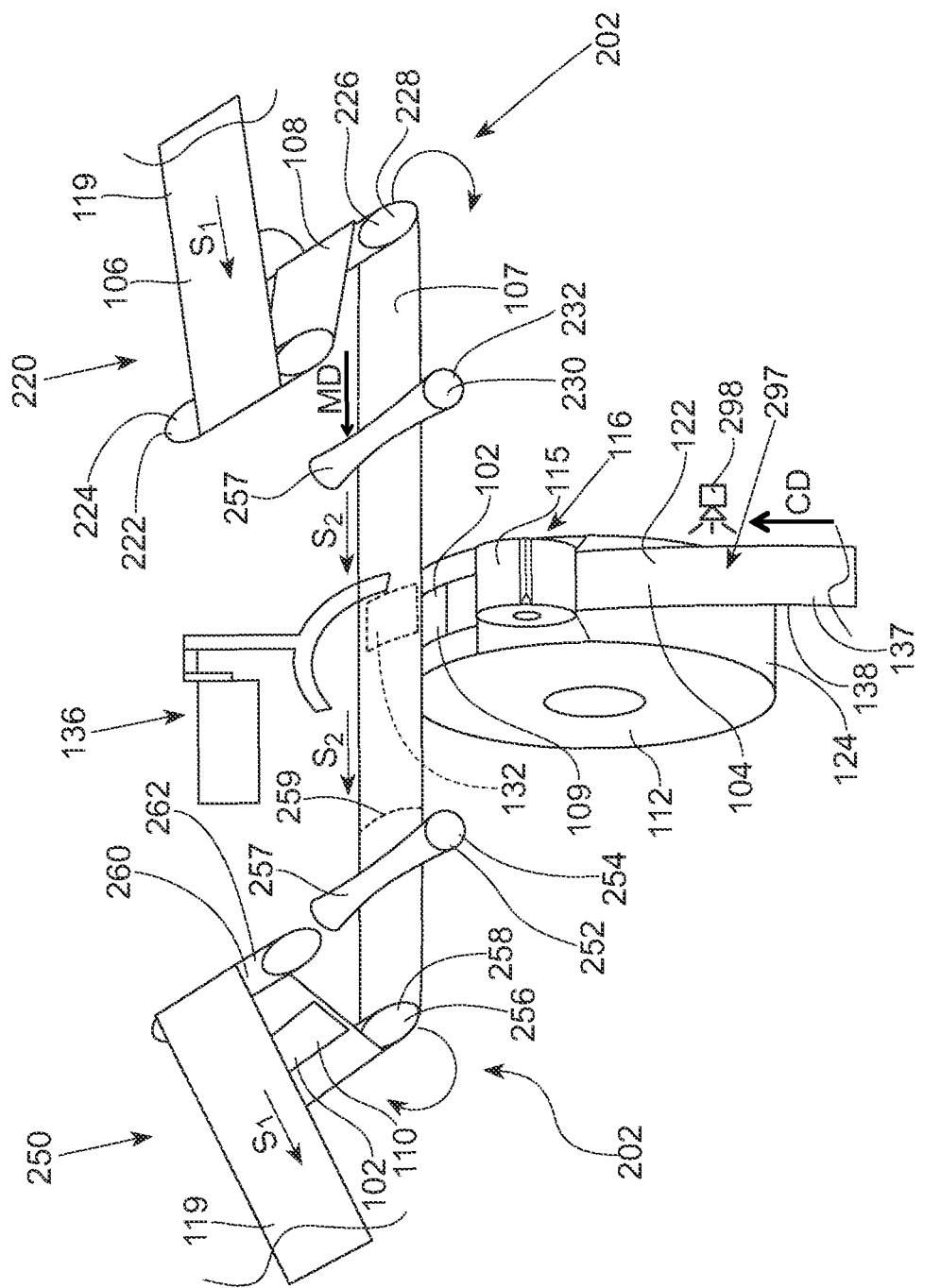
FIG. 4A is a schematic, perspective view of an apparatus for joining discrete lengths of a first substrate to a second substrate.

FIG. 4A shows an exemplary apparatus for joining a discrete length of elastic substrate 102 of a first substrate 104 to an advancing second substrate 106. The second substrate 106 is shown in FIG. 4A as a continuous length of absorbent articles 119 for illustrative purposes. It is to be appreciated that the continuous length of absorbent articles 119 may comprise various materials, including, for example, topsheet material, backsheet material, or combinations thereof. With reference to FIGS. 3A and 4A, the first substrate 104 may advance in a first direction, labeled as the cross direction CD, and a second substrate 106 may advance in a second direction, labeled as the machine direction MD. It is to be appreciated that the first substrate 104 advances in the cross direction CD relative to the machine direction MD of the advancing second substrate 106. The first substrate 104 may advance onto an outer circumferential surface 124 of the drum 112 in a stretched state. It is to be appreciated that the drum 112 of FIG. 4A may be used as the second metering device 300 shown in FIG. 3A.

Referring to FIG. 4A, the first substrate 104 may be defined by a first surface 137 and a second surface 138. The second substrate 106 may also be defined by a first surface 107 and a second surface 108. Adhesive 113 may be applied to the first surface 137 of the first substrate 104 before the first substrate 104 advances onto the drum 112. The first substrate 104 may be cut into discrete lengths of elastic substrate 102 by a cutter 116, shown in the form of a knife roll 115 for purposes of illustration, while advancing on the drum 112. The drum 112 may be configured with vacuum to hold the discrete lengths of elastic substrate 102 in a stretched state on the outer circumferential surface 124 of the drum 112 once the discrete length of elastic substrate 102 is cut from the first substrate 104. The discrete lengths of elastic substrate 102 may be defined by a first surface 109 and a second surface 110.

Concurrently, as the discrete lengths of elastic substrate 102 are advancing on the outer circumferential surface 124 of the drum 112, the second substrate 106 may advance in the machine direction MD by a conveyor 202 as shown in FIG. 4A. The conveyor 202 may position the second substrate 106 adjacent to, but not in contact with, the outer circumferential surface 124 of the drum 112. A tamper apparatus 136 is located adjacent to the drum 112 such that the discrete length of elastic substrate 102 and the second substrate 106 are positioned between the tamper apparatus 136 and the outer circumferential surface 124 of the drum 112. The tamper apparatus 136 may intermittently displace a target area 132 of the second surface of the second substrate 106 into contact with the first surface 109 of the discrete length of elastic substrate 102 on the outer circumferential surface 124 of the drum 112. As discussed in more detail below, the target area 132 of the second substrate may be deformed so as to define a curve in the cross direction CD that corresponds with at least a portion of the contour of the outer circumferential surface of the drum. The discrete length of elastic substrate 102 may be joined with the second substrate 106 and subsequently removed from the drum 112.

Figure 4B:
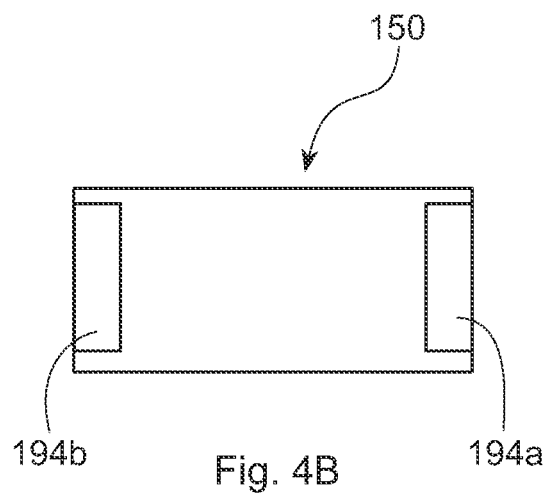
FIG. 4B is a schematic, plan view of a discrete absorbent article having a first waistband and a second waistband.
Figure 4C:
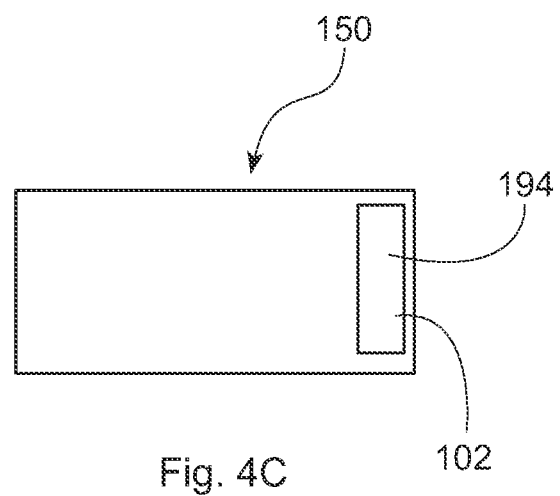
FIGS. 4C and 4D are schematic, plan views of a discrete absorbent article having a discrete waistband.
Figure 4D:
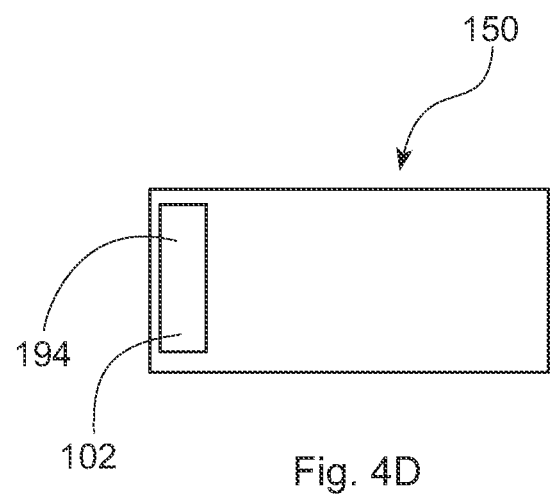

The second substrate 106 and the discrete length of elastic substrate 102 may continue advancing in the machine direction MD by the conveyor 202. In some exemplary configurations, vacuum may be intermittently interrupted in order to assist the discrete length of elastic substrate 102 in releasing from the drum 112. The process is repeated to bond each discrete length of elastic substrate 102 to the second substrate 106. As such, the discrete lengths of elastic substrate 102 are spaced apart in the machine direction MD on the second substrate 106. Subsequently, the second substrate 106 may be cut along the discrete length of elastic substrate 102 to form individual absorbent articles 150 having first and second waistbands 194a and 194b such as shown in FIG. 4B. In other exemplary configurations, the second substrate 106 may be cut into individual absorbent articles 150 before or after the discrete length of elastic substrate 102 to form absorbent articles 150 having one waistband 194 such as shown in FIGS. 4C and 4D.

While FIG. 4A shows adhesive 297 being applied to the first substrate 104 before the first substrate 104 advances onto the outer circumferential surface 124 of the drum 112, it is to be appreciated that adhesive 297 may be applied to the first substrate 104 while the first substrate 104 is advancing on the drum. In some exemplary configurations, the adhesive applicator 298 is configured to continuously apply adhesive 297 to the second surface 137 of the first substrate 104. It is to be appreciated that the adhesive can also be applied various different patterns. In some exemplary configurations, the adhesive 297 may be applied in the form of a spray. Various adhesive applicators may be used. For example, in some exemplary configurations, contact adhesive applicators (i.e. applicators that touch the substrate during adhesive application) such as slot coater adhesive applicators may be used. In other exemplary configurations, non-contact adhesive applicators (i.e. applicators that do not touch the substrate during adhesive application) such as spiral, meltblown, and omega adhesive applicators may be used. In other exemplary configurations, the first substrate 104 is pre-glued, so no additional adhesive is required to be added during the process.

Figure 5:
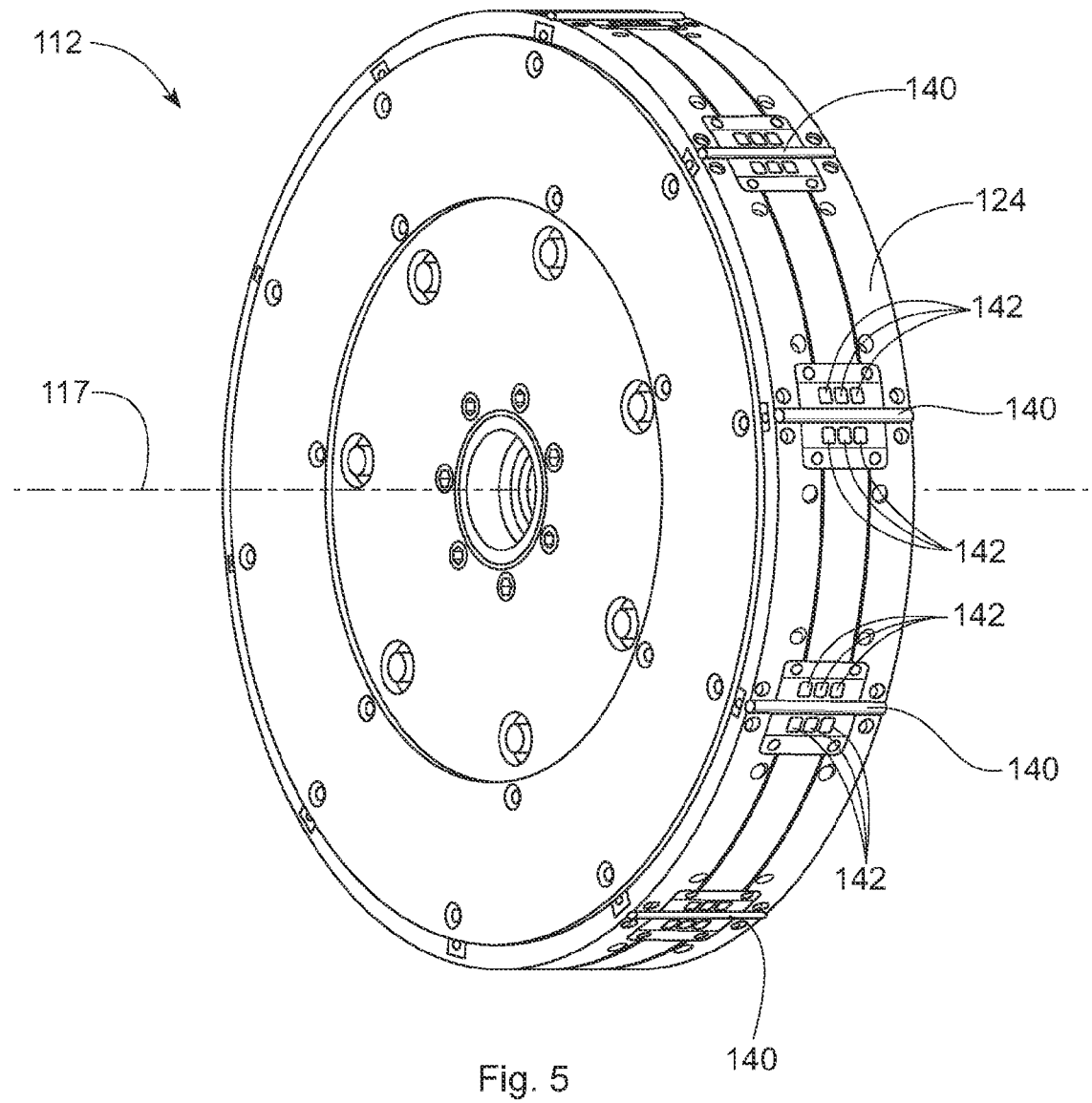
FIG. 5 is a schematic, perspective side view of a drum.

Referring to FIGS. 4A and 5, the drum 112 may include an outer circumferential surface 124 and may be rotatable about an axis of rotation 117. The outer circumferential surface 124 of the drum 112 may have a contour. The drum 112 may include anvils 140 for cutting the first substrate 104 into discrete lengths of elastic substrate 102 while advancing on the outer circumferential surface 124 of the drum 112. The anvils 140 may be capable of withstanding heat and pressure from the cutter 116. The anvils 140 may be spaced at predetermined locations around the outer circumferential surface 124 of the drum 112 for cutting the first substrate 104 into discrete lengths of elastic substrate 102 of a predetermined size. In addition, the outer circumferential surface 124 of the drum 112 may include vacuum apertures 142 for applying vacuum pressure to hold the discrete lengths of elastic substrate 102 in a stretched state on the outer circumferential surface 124 of the drum 112. The drum 112 may also be configured to intermittently stop rotating while the discrete lengths of elastic substrate 102 are being joined to the advancing second substrate 106. The drum 112 may be rotated in various ways including, for example, a servo motor or cam. The drum 112 may be configured for handling various size discrete lengths of elastic substrate. Exemplary rotary drums are described in U.S. Provisional Patent Application 61/665, 938, titled "Rotary Drum Apparatus Reconfigurable for Various Size Substrates," filed Jun. 29, 2012.

Figure 6A:
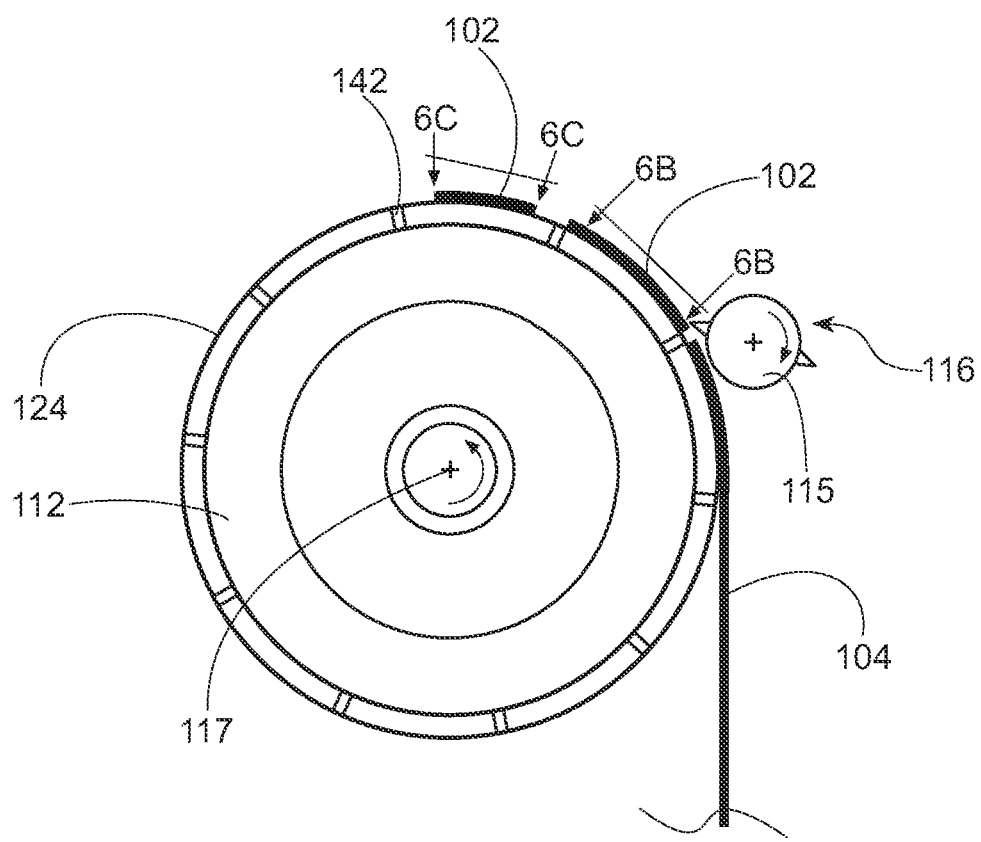
FIG. 6A is a schematic, side view of a process for cutting the first substrate into discrete lengths of elastic substrate and further consolidating the discrete lengths of elastic substrate to a reduced elongation.
Figure 6B:
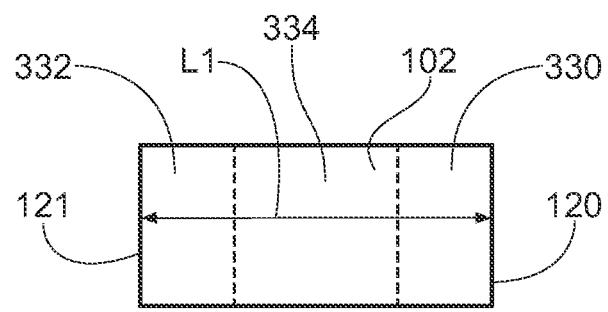
FIG. 6B is a discrete length of elastic substrate at a first elongation taken along line 6B-6B of FIG. 6A.

With reference to FIGS. 6A and 6B, the drum 112 may be configured to apply vacuum pressure to the first, second, and central regions 130, 132, and 134 of the discrete length of elastic substrate 102 to hold the discrete length of elastic substrate 102 in a stretched state. It is to be appreciated that to hold the discrete lengths of elastic substrate 102 on the outer circumferential surface 124 of the drum 112, the vacuum pressure is reduced below atmospheric pressure. Different vacuum pressures may be needed to hold different discrete lengths of elastic substrate 102 on the outer circumferential surface 124 of the drum 112. For example, a discrete length of elastic substrate stretched to relatively high percent elongation may require a lower vacuum pressure than a discrete length of elastic substrate stretched to a lower percent elongation. In addition, a discrete length of elastic substrate having a higher decitex elastic material may require a lower vacuum pressure than a discrete length of elastic substrate having a lower decitex elastic material. Also, a discrete length of elastic substrate having a greater number of elastic strands may require a lower vacuum pressure than a discrete length of elastic substrate having fewer elastic strands.

Referring to FIG. 6B, the discrete length of elastic substrate 102 may be defined by a first end region 330, a second end region 332, and a central region 334 separating the first and second end regions 330 and 332. The discrete lengths of elastic substrate 102 may have a first length L1 extending from the first end 120 to the second end 121 of the discrete length of elastic substrate 102. The discrete length of elastic substrate 102 may be stretched to a first elongation and have a first length L1 when the discrete length of elastic substrate 102 is cut from the first substrate 104. It is to be appreciated that FIG. 6B is a view taken along line 6B-6B from FIG. 6A.

Figure 6C:
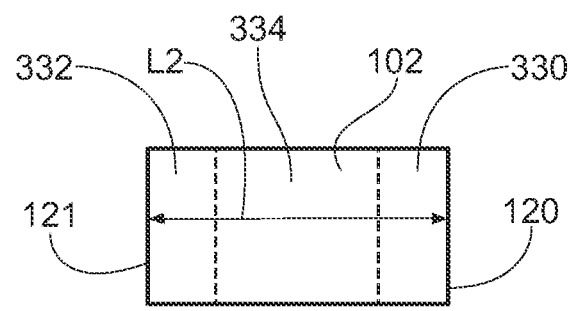
FIG. 6C is a discrete length of elastic substrate at a second elongation taken along line 6C-6C of FIG. 6A.

With reference to FIGS. 6A and 6C, the drum 112 may be configured to increase the vacuum pressure on the first and second end regions 330 and 332 to consolidate the discrete length of elastic substrate 102. As a result of the increased vacuum pressure on the first and second end regions 330 and 332 of the discrete length of elastic substrate 102, the first and second end regions 330 and 332 consolidate. In turn, the discrete length of elastic substrate 102 consolidates from a first elongation to a second elongation and from the first length L1 to a second length L2 that is shorter than the first length L1. It is to be appreciated that FIG. 6C is a view taken along line 6C-6C from FIG. 6A. In some exemplary configurations, a first vacuum pressure may be applied to the first end region 330, a second vacuum pressure may be applied to the second end region 332, and a third vacuum pressure may be applied to the central region 334. In some exemplary configurations, the first and second vacuum pressures may be increased above the third vacuum pressure such that the first and second end regions 330 and 332 of the discrete length of elastic substrate contract and the central region 334 remains at least partially stretched. The discrete length of elastic substrate 104 may have a first elongation of about 150% at the first length L1 and a second elongation of about 80% at the second length L2. Exemplary methods and apparatuses for consolidating layered elastic substrates are described in U.S. Provisional Patent Application 61/665,933, titled "Methods and Apparatuses for Consolidating Elastic Substrates," filed Jun. 29, 2012.

Referring back to FIG. 4A, the conveyor may be in the form of a localized speed varying apparatus 202. The localized speed varying apparatus 202 may slow or stop the movement of the second substrate 106 adjacent to the drum 112 while maintaining the second substrate 106 at a constant speed upstream and downstream of the drum 112. The localized speed varying apparatus 202 advances the second substrate 106 in the machine direction MD through a first substrate guide 220 at a first speed $S_1$. The second substrate 106 advances from the first substrate guide 220 at a second speed $S_2$ as the second substrate 106 advances adjacent the drum 112. Once the second substrate 106 advances past the drum 112, the second substrate 106 enters a second substrate guide 250. The second substrate 106 then exits the second substrate guide 250 at the first speed $S_1$. As discussed in more detail below, the first substrate guide 220 and second substrate guide 250 operate to change the lengths of the second substrate 106 within the respective guides 220, 250, and thus, vary the second speed $S_2$ of the second substrate 106 traveling from the upstream, first substrate guide 220 to the downstream, second substrate guide 250. At the same time, the speed of the second substrate 106 entering the first substrate guide 220 and exiting the second substrate guide 250 is maintained at a constant first speed $S_1$.

As previously mentioned, the second speed $S_2$ of the second substrate 106 can be varied as the second substrate 106 travels from the first substrate guide 220 to the second substrate guide 230 adjacent the drum 112. The first and second substrate guides 220, 250 may be configured to periodically slow (e.g. second speed, $S_2$, is slower than the first speed, $S_1$) the movement of the second substrate 106 in the machine direction MD passing adjacent the drum 112. In some configurations, the first and second substrate guides 220, 230 may be configured to periodically stop (e.g. second speed, $S_2$, is zero) the movement of the second substrate 106 in the machine direction MD passing adjacent the drum 112. In yet other configurations, the first and second substrate guides 220, 250 may be configured to periodically reverse the movement of the second substrate 106 (e.g. second substrate moves upstream relative to the machine direction MD) while passing adjacent the drum 112.

As shown in FIG. 4A, the first substrate guide 220 includes a first guide member 222 in the form of a first roller 224, a second guide member 226 in the form of a second roller 228, and a third guide member 230 in the form of a third roller 232. As described below, the substrate 106 travels in the machine direction MD at the first speed $S_1$ to the first roller 224; from the first roller 224 to the second roller 228; from the second roller 228 to the third roller 232; and from the third roller 232 to the second substrate guide 240 at the second speed $S_2$. As shown in FIG. 1, the first roller 224 defines an outer radial surface 234 and rotates around a first center axis 236. The second roller 228 defines an outer radial surface 238 and is rotatably connected with a support member 240 at a second roller axis 242. The support member 240 is adapted to rotate around a second center axis 242. As such, the second roller 228 orbits around the second center axis 242 as the support member 240 rotates. The third roller 232 defines an outer radial surface 244 and rotates around a third center axis 246.

Similar to the first substrate guide 220, the second substrate guide 250 includes a first guide member 252 in the form of a first roller 254, a second guide member 256 in the form of a second roller 258, and a third guide member 260 in the form of a third roller 262. As described below, the second substrate 106 travels in the machine direction MD at the second speed $S_2$ (from the first substrate guide 220) to the first roller 254; from the first roller 254 to the second roller 258; from the second roller 258 to the third roller 262; and from the third roller 262 to continue downstream at the first speed $S_1$. As shown in FIG. 4A, the first roller 254 defines an outer radial surface 264 and rotates around a first center axis 266. The second roller 258 defines an outer radial surface 268 and is rotatably connected with a support member 270 at a second roller axis 272. The support member 270 is adapted to rotate around a second center axis 274. As such, the second roller 258 orbits around the second center axis 274 as the support member 270 rotates. The third roller 262 defines an outer radial surface 276 and rotates around a third center axis 278.

As shown in FIG. 4A, the third roller 232 of the first guide member 222 and first roller 258 of the second guide member 250 have curved outer surfaces 257. In addition, the outer circumferential surface 124 of the drum 112 defines a contour that may be curved. As shown in FIG. 4A, the curved shape of the outer surface 257 of the third roller 232 and the first roller 258 corresponds with at least a portion of the contour of the outer circumferential surface 124 of the drum 112. As a result, the curved shape of the outer surface 257 of the third roller 232 deforms the second substrate 106 in the cross direction CD to define a curve 259 extending along the cross direction CD as the second substrate 106 is adjacent to the outer circumferential surface 124 of the drum 112. The curve 259 of the second substrate 106 defines a shape that corresponds with a portion of the contour of the outer circumferential surface 124 of the drum 112. Deforming the substrate 106 adjacent to the drum 112 with the third roller 232 may also help the substrate bond more completely along the discrete length of elastic substrate 102. In some exemplary configurations, some or all of the rollers of the first and second guide members 220, 250 may have a curved outer surface corresponding with at least a portion of the contour of the outer circumferential surface 124 of the drum 112 to help the second substrate 106 bond more precisely and/or completely to the discrete length of elastic substrate 102.

While the conveyor is shown in FIG. 4A as a localized speed varying apparatus, various other conveyors for slowing or stopping the movement of the second substrate are described in U.S. Pat. Nos. 5,693,165 and 6,596,108; and U.S. Publication No. 2010/0252603.

Figure 7:
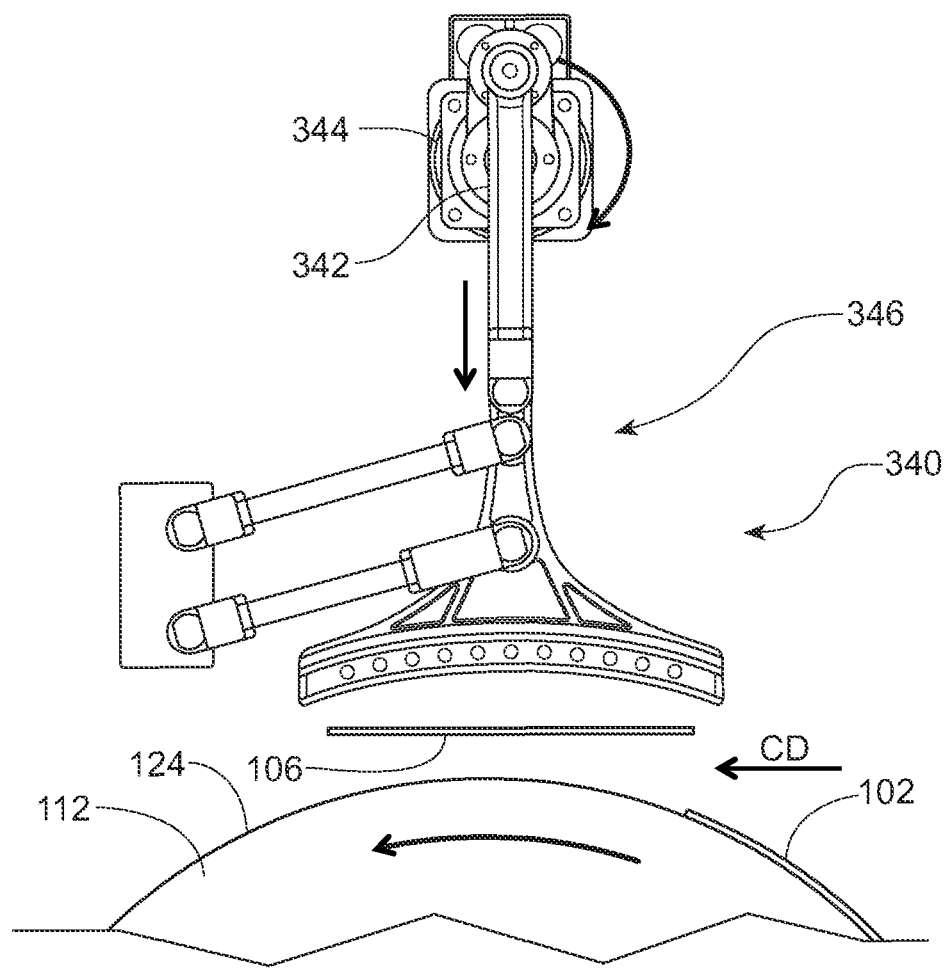
FIG. 7 is a schematic, elevation view of a tamper apparatus having a tamper member in a first position.
Figure 8:
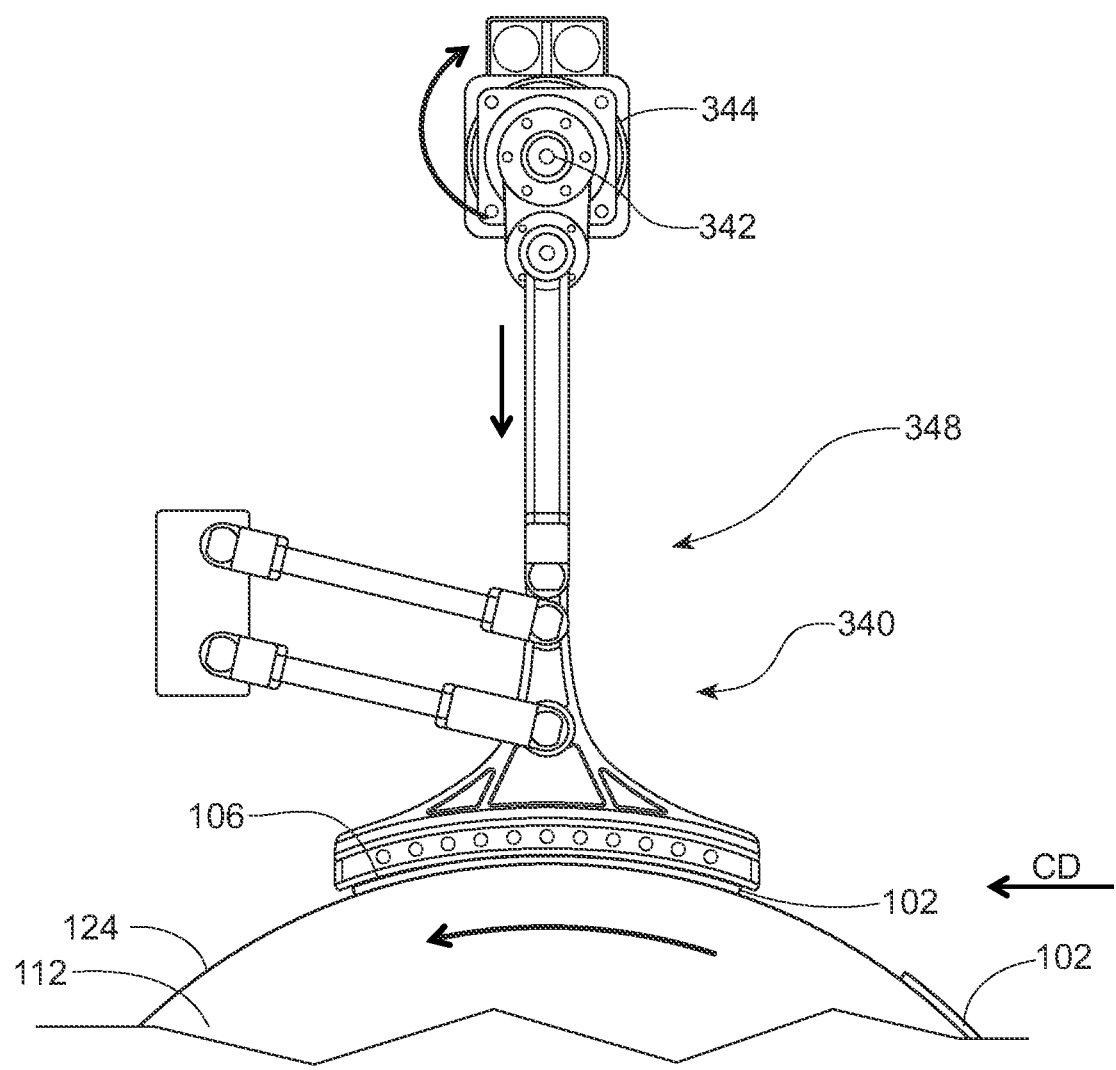
FIG. 8 is a schematic, elevation view of a tamper apparatus having a tamper member in a second position.

As shown in FIG. 7, the tamper apparatus 136 may be located adjacent to the drum 112 such that the discrete length of elastic substrate 102 and the second substrate 106 are positioned between the drum 112 and the tamper apparatus 136. The tamper apparatus 136 may include a tamper member 340 associated with a shaft 342 of a servo motor 344. The shaft 342 of the motor 344 is configured to continuously rotate in a single direction. The servo motor 344 may be configured to rotate the shaft 342 in a first phase and a second phase. When the shaft rotates in the first phase, the tamper member travels from a first position 346 shown in FIG. 7 to a second position 348 shown in FIG. 8 to intermittently displace a target area 132 of the deformed portion of the second substrate 106 into contact with the discrete length of elastic substrate 102 on the drum 112. In particular, the tamper member 340 engages a first surface 107 of the second substrate 106 and moves a second surface 109 of the second substrate 106 toward the outer circumferential surface 124 of the drum 112. When the shaft 342 rotates in the second phase, the tamper member 340 travels from the second position 348 to the first position 346 to move away from the second substrate. Exemplary tamper apparatuses are described in U.S. Provisional Patent Application 61/665,928, titled "Method and Apparatus for Attaching Components to Absorbent Articles," filed Jun. 29, 2012. It should also be appreciated that the apparatuses and methods described herein can utilize various types of transfer apparatuses other than the tamper apparatus described above. Exemplary transfer apparatuses are described in U.S. Patent Publication No. US 2009/0294004, published on Dec. 3, 2009.

Figure 9:
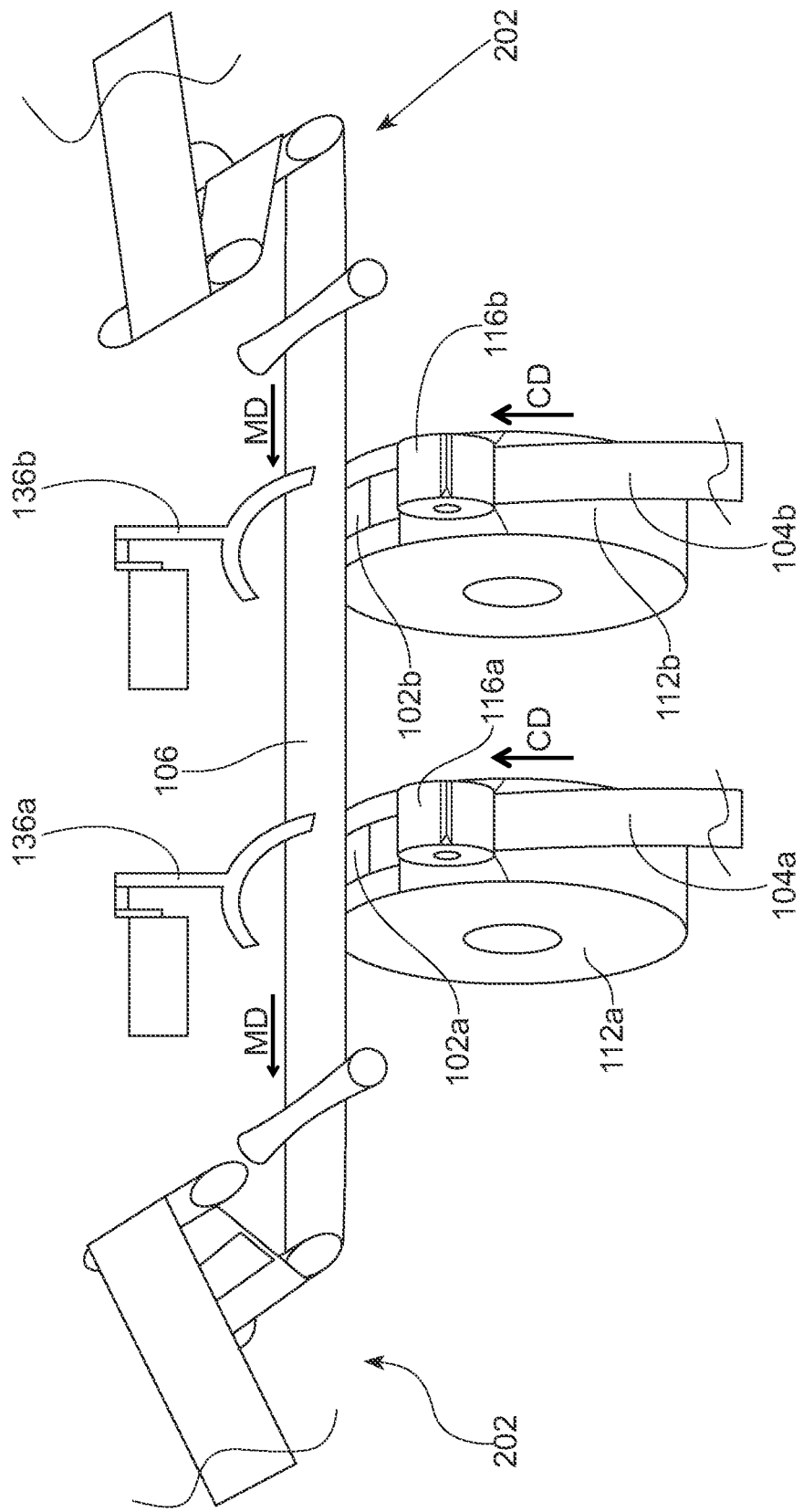
FIG. 9 is a schematic, perspective view of an apparatus for joining discrete lengths of a first substrate to a second substrate having two drums and two tamper apparatuses.

As shown in FIG. 9, two continuous lengths of first substrate may advance onto two drums such that two discrete bands may be applied to the second substrate at a time. A first substrate 104a and a first substrate 104b may advance onto drums 112a and 112b, respectively. A cutter 116a and a cutter 116b cut first substrates 104a, 104b into discrete lengths of elastic substrate 102a, 102b. Once the discrete lengths of elastic substrate 102a, 102b are cut, a tamper apparatus 136a and a tamper apparatus 136b direct the second substrate 106 toward the drum so as to bond the discrete lengths of elastic substrate 102a, 102b to the second substrate 106. Thus, the process can operate at high speeds as two discrete lengths of elastic substrate 102a, 102b may be applied to the second substrate 106 while the localized speed varying apparatus 202 may stop the second substrate 106 in the machine direction MD.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for applying discrete lengths of a first substrate to a second substrate, the method comprising the steps of:
   rotating a drum about an axis of rotation, the drum having an outer circumferential surface, wherein the outer circumferential surface has a contour;
   advancing a first substrate in a first direction;
   stretching the first substrate along the first direction;
   advancing the stretched first substrate onto the outer circumferential surface of the drum;
   cutting the stretched first substrate into discrete lengths of substrate while advancing on the outer circumferential surface of the drum, wherein each discrete length includes a first end region, a second end region, and a central region separating the first and second end regions;
   advancing a second substrate in a second direction, wherein the second direction crosses the first direction;
   advancing the second substrate over a roller, the roller having an outer surface, wherein the outer surface of the roller has a curved shape, and wherein the curved shape of the outer surface of the roller corresponds with at least a portion of the outer circumferential surface of the drum;
   deforming a portion of the second substrate along the first direction to define a curve extending along the first direction, wherein the curve corresponds with at least a portion of the outer circumferential surface of the drum;
   repeatedly displacing the deformed portion of the second substrate into contact with the discrete lengths of substrate on the outer circumferential surface of the drum; and bonding the discrete lengths of substrate to the second substrate.

2. The method of claim 1, wherein the step of deforming further comprises advancing the second substrate by a conveyor.

3. The method of claim 1 further comprising the step of stopping the second substrate from advancing in the second direction prior to the step of displacing the deformed portion of the second substrate into contact with the discrete length of substrate on the outer circumferential surface of the drum.

4. The method of claim 1 wherein the step of repeatedly displacing the deformed portion of the second substrate into contact with the discrete length of substrate further comprises the steps of:
 continuously rotating a shaft of a motor at a variable angular velocity in a single direction, wherein the motor is configured to rotate the shaft in a first phase and a second phase, wherein the shaft of the motor is associated with a tamper member;
 shifting the tamper member from a first position to a second position toward the second substrate and the outer circumferential surface of the drum as the shaft of the motor rotates in the first phase.

5. The method of claim 4, wherein the variable angular velocity of the shaft of the motor increases in the first phase.

6. The method of claim 4, wherein the variable angular velocity of the shaft of the motor decreases in the second phase.

7. The method of claim 1 further comprising the steps of:
 advancing a first substrate layer in a machine direction through a nip, the first substrate layer having a first surface and an opposing second surface;
 advancing a second layer substrate layer in the machine direction through the nip, the second substrate layer having a first surface and an opposing second surface;
 advancing an elastic material in a stretched state in the machine direction through the nip;
 bonding the elastic material in the stretched state to the first surface of the first substrate layer and the first surface of the second substrate layer thereby forming the first substrate.

8. The method of claim 7 further comprising the steps of:
 advancing the first substrate through a first metering device at speed, V1;
 advancing the first substrate through a second metering device at speed, V2, subsequent to advancing through the first metering device, wherein V1 is greater than V2;
 stretching the elastic material to a first elongation at the first metering device; and
 consolidating the first substrate to a second elongation at the second metering device.

9. The method of claim 7, wherein the first elongation is about 150% and the second elongation is about 80%.

10. The method of claim 7, wherein the first and second substrate layers are formed from a single continuous substrate.

11. The method of claim 1 further comprising the step of applying vacuum pressure to the outer circumferential surface of the drum to hold the discrete lengths of substrate in a stretched state.

12. The method of claim 11 further comprising the steps of:
 applying vacuum pressure to the first end region, second end region, and central region of the discrete length of substrate, wherein the vacuum pressure is below atmospheric air pressure; and
 changing the vacuum pressure on the first and second end regions such that the discrete length of substrate consolidates to a second length less than the first length.

13. The method of claim 12, further comprising the step of:
 applying a first vacuum pressure to the first end region, applying a second vacuum pressure to the second end region, and applying a third vacuum pressure to the central region.

14. The method of claim 12, further comprising the step of:
 increasing the first and second vacuum pressure above the third vacuum pressure.

15. The method of claim 1, wherein the discrete lengths of substrate are spaced apart from each other along the second direction, and further comprising the step of cutting the second substrate to separate the substrate into discrete diapers.

16. The method of claim 15, wherein the step of cutting the second substrate further comprises cutting the second substrate along the discrete length of substrate to create a first discrete diaper having a first elastic waistband and a second discrete diaper having a second elastic waistband.

17. The method of claim 1, wherein the discrete length of substrate is an elastic waistband.

* * * * *